US00PP24561P3

(12) United States Plant Patent
Scheffers

(10) Patent No.: US PP24,561 P3
(45) Date of Patent: Jun. 17, 2014

(54) *SANSIEVERIA* PLANT NAMED 'SAN201201'

(50) Latin Name: *Sansieveria ehrenbergii*
Varietal Denomination: SAN201201

(75) Inventor: Johannes Scheffers, Honselersdijk (NL)

(73) Assignee: Kwekerij Zeurniet (NL)

( * ) Notice: Subject to any disclaimer, the term of this patent is extended or adjusted under 35 U.S.C. 154(b) by 92 days.

(21) Appl. No.: 13/573,343

(22) Filed: Sep. 10, 2012

(65) Prior Publication Data

US 2014/0075627 P1 Mar. 13, 2014

(51) Int. Cl.
*A01H 5/00* (2006.01)

(52) U.S. Cl.
USPC ..... Plt./382; Plt./373

(58) Field of Classification Search
USPC ..... Plt./373, 382
See application file for complete search history.

*Primary Examiner* — Susan McCormick Ewoldt
(74) *Attorney, Agent, or Firm* — Cassandra Bright

(57) ABSTRACT

A new and distinct *Sanseveria* cultivar named 'SAN201201' is disclosed, characterized by short, thick, dark green leaves with a silver hue. Plants are compact with uniformly spaced and angled foliage, occurring from completely upright to nearly horizontal. The new variety is a *Sanseveria,* typically produced as an ornamental plant.

1 Drawing Sheet

Latin name of the genus and species: *Sansieveria ehrenbergii.*

Variety denomination: 'SAN201201'.

BACKGROUND OF THE INVENTION

The new cultivar is the product of a planned breeding program, with the intention to develop new interesting *Sansieveria* varieties for ornamental purposes. The new variety was discovered as a seedling, resulting from the crossing of unnamed, unpatented varieties of *Sanseveria ehrenbergii* during 2007. Seed was bulk collected, with the exact parentage unidentifiable.

The new variety was discovered by the inventor, Johannes Wilhelmus Maria Scheffers, a citizen of the Netherlands, during 2008, in a commercial greenhouse in Bangkok, Thailand. After identifying the new variety as a potentially interesting selection, the inventor continued confidential testing and propagation of 'SAN201201', assessing the stability of the unique characteristics of this variety.

Asexual reproduction of the new cultivar 'SAN201201' was first performed at the commercial greenhouse in Bangkok, Thailand during 2008 by separation of vegetative suckers from the original plant. Access to all plants was restricted, as plants were kept in a greenhouse not open to the public. Through subsequent propagation by vegetative suckers, multiple generations have been reproduced, which have shown that the unique features of this cultivar are stable and reproduced true to type.

SUMMARY OF THE INVENTION

The cultivar 'SAN201201' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SAN201201'.

These characteristics in combination distinguish 'SAN201201' as a new and distinct *Sansieveria* cultivar:

1. Compact plant shape.
2. Nearly entire foliage margin
3. Short foliage
4. Thick foliage.
5. Green foliage with a strong bluish grey hue.

COMPARISON TO KNOWN VARIETIES

Plants of the new cultivar 'SAN201201' are similar to the unnamed, unpatented *Sansieveria ehrenbergii* available commercially in Europe and the United States, in most horticultural characteristics. The new variety, however, produces leaves which are green in color with a strong bluish grey hue, whereas the commercially known variety produces leaves that are green with silvery hue. The leaves of 'SAN201201' are thicker, and shorter than foliage of the known commercial variety, forming an overall more compact plant shape for the new variety.

BRIEF DESCRIPTION OF THE PHOTOGRAPH

The accompanying photograph in FIG. 1 illustrates in full color a typical plant of 'SAN201201' grown in a commercial greenhouse in Honselersdijk, The Netherlands. This plant is approximately 2 years old, shown planted in a 17 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SAN201201' plants grown outdoors at a nursery in Honselersdijk, The Netherlands, under 50% shade cloth. The temperature range was approximately 17° to 30° C. at night and 22° to 40° C. during the day. No artificial light, or photoperiodic treatments were given to the plants. Measurements and numerical values represent averages of typical plant types.

Botanical classification: *Sansieveria ehrenbergii* 'SAN201201'.

PROPAGATION

Time to initiate rooting: About 2-3 months at approximately 17° to 40° C.

Root description: Thick, fleshy, slightly fibrous, not dense, moderately branched colored greyed-orange, near RHS 165D.

PLANT

Age of plant described: 2 years.

Pot size of plant described: 17 cm pot.

Growth habit: Monopodial, distichous.

Height: Approximately 9.5 cm.

Plant spread: Approximately 30.5 cm at widest and approximately 4.0 cm at narrowest.

Growth rate: Slow. Approximately 2 cm per month.

Number of leaves per plant of the above age: Average: 4.

FOLIAGE

Leaf:

*Arrangement.*—Distichous.

*Average length.*—Approximately 16.1 cm (incl. sheath).

*Average width.*—Approximately 4.0 cm.

*Depth of leaf blade.*—Approximately 3.9 cm.

*Shape of blade.*—Lanceolate, strongly carinate and very succulent.

*Aspect.*—Leaves grow in an average angle of 25° to soil level (=0°=horizontal).

*Apex.*—Apiculate with a pungent tip.

*Base.*—Decurrent.

*Margin.*—Entire, very slightly angulate.

*Texture of top surface.*—Smooth, very slightly glossy.

*Texture of bottom surface.*—Smooth, very slightly glossy.

*Color.*—Young foliage upper side: Greyed-green, near RHS 189A, tip greyed-orange, near RHS 172A. Young foliage under side: Greyed-green, near RHS 189A, tip greyed-orange, near RHS 172A. Mature foliage upper side: Greyed-green, near RHS 189A, tip greyed-orange, near RHS 172C, outer (pungent) tip grey-brown; near RHS 199B; margins greyed-orange; near RHS N170C. Mature foliage under side: Greyed-green, near RHS 189A, tip greyed-orange, near RHS 172C, outer (pungent) tip grey-brown; near RHS 199B; margins greyed-red, near RHS 178A, outer margins greyed-orange; near RHS N170C.

*Venation.*—Type: Parallel. Color: Upper side: No veins visible on upper side. Under side: Veins barely visible, colored greyed-green, near RHS N189B.

Sheath:

*Average length.*—Approximately 0.4 cm.

*Average width.*—Approximately 0.7 cm.

*Color.*—Greyed-orange; near RHS 175A.

*Texture.*—Smooth, slightly glossy.

OTHER CHARACTERISTICS

Flower production: Not observed.

Disease resistance: Neither resistance nor susceptibility to normal diseases and pests of *Sansieveria* has been observed.

Drought tolerance and temperature tolerance: Plants are drought tolerant, and easily tolerate high temperatures to at least 40° C.

Fruit/seed production: Not observed.

What is claimed is:

1. A new and distinct cultivar of *Sanseveria* plant named 'SAN201201' as herein illustrated and described.

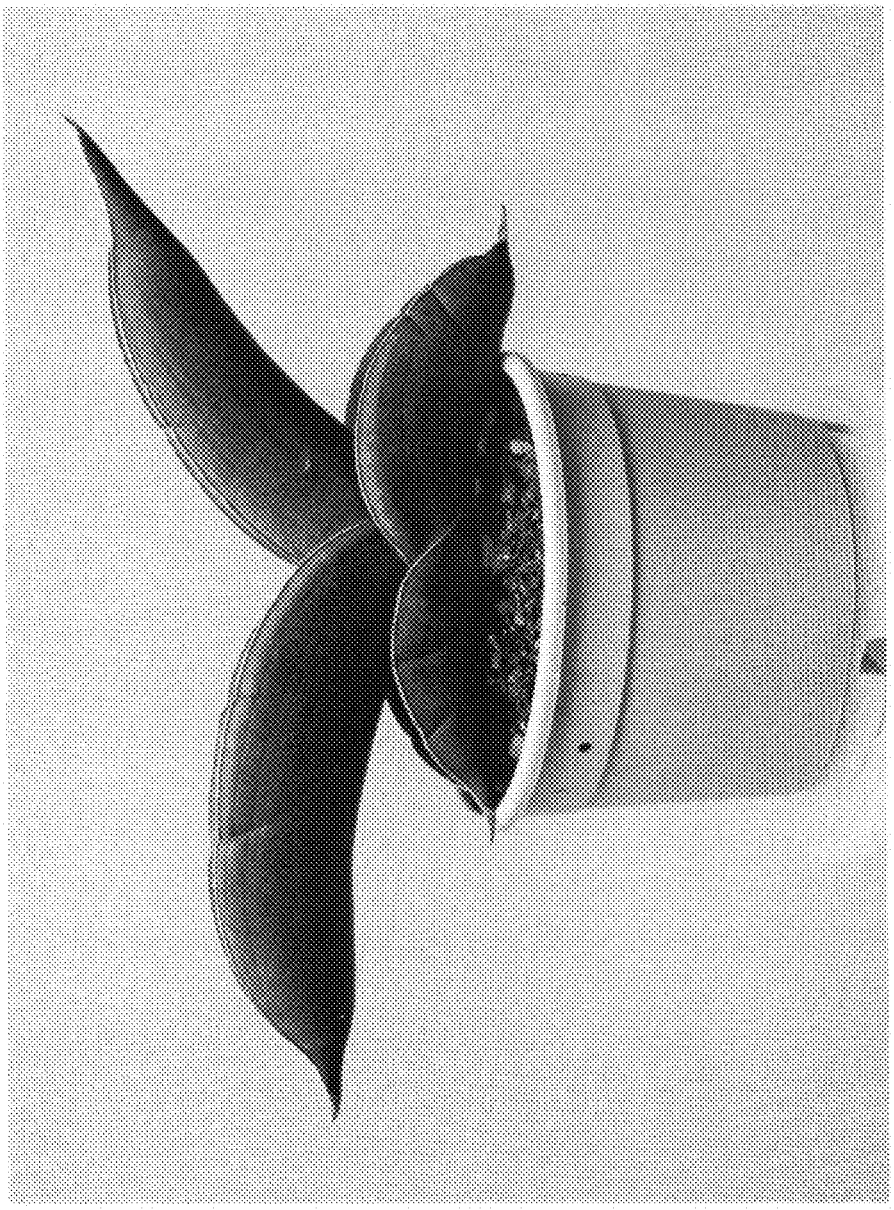

* * * * *